(12) United States Patent
Fay et al.

(10) Patent No.: US 8,524,814 B2
(45) Date of Patent: Sep. 3, 2013

(54) PHOSPHONATE BONDING COMPOSITIONS

(75) Inventors: Nigel Fay, Kildare (IE); Eimear M. Fleming, Dublin (IE); Darren Nolan, Dublin (IE); Brendan J. Kneafsey, Dublin (IE)

(73) Assignee: Henkel Ireland Limited, Monheim (DE)

( * ) Notice: Subject to any disclaimer, the term of this patent is extended or adjusted under 35 U.S.C. 154(b) by 0 days.

(21) Appl. No.: 13/446,680

(22) Filed: Apr. 13, 2012

(65) Prior Publication Data
US 2012/0202091 A1 Aug. 9, 2012

Related U.S. Application Data

(63) Continuation of application No. PCT/EP2010/063575, filed on Sep. 15, 2010.

(60) Provisional application No. 61/243,665, filed on Sep. 18, 2009.

(51) Int. Cl.
*C08K 5/00* (2006.01)

(52) U.S. Cl.
USPC ........ 524/123; 428/704; 156/330.9; 156/153; 558/176; 558/158; 528/399; 106/287.23

(58) Field of Classification Search
USPC ....................................... 524/123
See application file for complete search history.

(56) References Cited

U.S. PATENT DOCUMENTS

| 3,632,758 A | 1/1972 | Partos et al. |
| 4,031,120 A | 6/1977 | Gervase |
| 2009/0181248 A1 | 7/2009 | Van Ooij et al. |

FOREIGN PATENT DOCUMENTS

| CA | 1087774 | 10/1980 |
| WO | 0026219 | 5/2000 |
| WO | 2004078867 | 9/2004 |

OTHER PUBLICATIONS

International Search Report issued in connection with International Patent Application No. PCT/EP2010/063575 mailed Feb. 18, 2011.
Albrecht B. et al., "In vivo utilization of n-(phosphonomethyl)-anilines and related substances by pseudomonas spec. GS", Journal of Basic Microbiology, Wiley—VC H Verlag GmbH & Co. KGaA, Berlin, DE vol. 31, No. 6, pp. 403-411 (1991) (XP000901968).
Bogdanov et al., "Reaction of diethyl phosphite with 1,2-naphthoquinone" (XP002620972).
Kukhtin et al., "Some new types of the Arbuzov rearrangement. XIII. Reaction of trialkyl phosphites with o- and p-nitrobenzaldehydes" (XP002620973).
Metcalf et al "Para-substituted meta-xylenyl diethyl phosphates and N-methylcarbamates as anticholinesterases and insecticides" (XP002620974).
Kutyrev et al., "Phosphorylated hydrazones of p-benzoquinone" (XP002620975).
Wynberg et al., "Asymmetric catalysis in carbon-phosphorus bond formation", (XP002620976).
Corrie et al., "Photochemistry and thermal decarboxylation of alpha-phosphoryloxy-p-nitrophenylacetates" (XP002620977).
Mukmeneva et al., "Reaction of 3,5-di-tert-butyl-4-hydroxybenzyl acetate with trialkyl phosphites" (XP002620980).
Kutyrev et al., "Two reactions of phosphoric acid hydrazides with p-benzoquinones" (XP002620981).

*Primary Examiner* — Doris Lee
(74) *Attorney, Agent, or Firm* — Steven C. Bauman

(57) ABSTRACT

The present invention provides for compounds comprising at least one phosphonate or phosphinate moiety; and at least one moiety selected from an aromatic nitroso or an aromatic nitroso precursor and combinations thereof. Adhesive compositions comprising the compounds may find utility in bonding polymers to metal and or hydroxylated surfaces such as glass. Suitable polymers include natural and synthetic rubbers. The aromatic nitroso precursor may be a nitrosobenzene precursor such as at least one of a quinone dioxime or a quinone oxime.

13 Claims, No Drawings

PHOSPHONATE BONDING COMPOSITIONS

BACKGROUND

1. Field

The present invention provides for phosphonate bonding compositions. In particular, the present invention provides for phosphonate bonding compositions useful in bonding polymers to substrates such as metals or glass.

2. Brief Description of Related Technology

Reinforced composite materials play a critical role in the manufacture of high-performance products that need to be lightweight, yet strong enough to take harsh loading and operating conditions. Popular reinforcing materials included wood, glass, metals, quartz and carbon fibres. Composites reinforced with such materials may find utility in the manufacture of a number of structural materials such as aerospace components and racing car bodies.

Polymer to metal and in particular rubber to metal bonding has been practised for many years. There are many applications for formulations which achieve polymer or rubber to metal bonding. Rubber to metal bonding is widely used to bond different metals to a natural or synthetic rubber so as to combine the structural strength of the metal with the elastomeric properties of the rubber.

Accordingly, metal and polymers such as rubber are often bonded to each other for impact absorption applications, such as in bearings, wheels, shock absorbers, moving arms, etc. Such components can be utilised on a very small scale, for example in PC components or on a very large scale for example in constructions such as bridges and buildings. Noise reduction may also be achieved by utilising metal to rubber bonding. It is accepted that tremendous forces can be experienced by any component that comprises metal and rubber bonded together. Thus, it is desirable to provide metal to rubber bonding, which can withstand significant forces, such as compressive or extensive pressures including shocks without having the metal or the rubber separate from each other. There are many other rubber to metal bonding applications, including tyre production where internal wire reinforcements for the tyre are bonded to the rubber of the tyre. Prior art compositions are discussed below.

Glass fibre reinforced composite materials consist of high strength glass fibres embedded in a matrix. For example, Glass Fibre Reinforced Concrete comprises glass fibres embedded in cement-based matrix and may find utility in buildings and other structural edifices. Similarly, Glass Reinforced Plastic comprises glass fibres embedded in a plastic material. Glass Reinforced Plastics are immensely versatile materials which combine to provide lightweight materials with high strength performance. Glass reinforced plastics find utility in a number of different areas from structural engineering to telecommunications.

Elastomer to glass bonding provides an attractive means by which the structural strength of glass can be combined with the elastomeric properties of the elastomer/rubber. Reinforcing fibres such as glass fibres have been used as a reinforcing material for rubber articles such as in rubber belts, tyres and hoses. In particular, glass fibres have been employed to reinforce automotive timing belts, where there is a need for synchronous transfer of power from crankshaft to overhead camshaft without loss of inertia.

Traditionally, such glass cord composites are manufactured by coating individual filaments of glass yarn with specialised coatings, such as resorcinol formaldehyde latex ("RFL") formulations. Conventional rubber to metal bonding products are then employed to bond the RFL latex to the rubber via a vulcanisation step.

Traditional rubber-to-metal bonding technology incorporates a two-step system, where in a first step a primer is applied and thereafter in a second step an adhesive is applied. The primer ordinarily consists of solutions or suspensions of chlorinated rubber and phenolic resins containing reactive groups, and also pigments such as titanium dioxide, zinc oxide, carbon black, etc. The primer is generally applied as a thin layer onto a treated (cleaned) surface of a metallic component such as treated steel component for example a component that has been grit blasted or chemically treated.

The adhesive ordinarily consists of a large range of rubber materials and cross-linkers. These include, but are not restricted to, chlorinated and bromochlorinated rubbers, aromatic nitrosobenzene compounds and bismaleimide as cross-linkers, xylene, perchloroethylene and ethylbenzene as solvents, and also some lead or zinc salts. The adhesive layer is generally the link between the primed metal and the rubber. Other cross-linkers that have been employed in rubber-to-metal bonding technology are aromatic nitroso compounds, such as p-dinitrosobenzene.

Many formulations for rubber to metal bonding exist. For example silanes have been used as corrosion inhibitors and as rubber-to-metal bonding adhesion promoters. U.S. Patent Application Publication No. 2009/0181248 discloses substantially hydrolysed silane solutions, for example bis(trimethoxypropyl)amine and bis(triethoxypropyl)tetrasulfide, for use in a rubber to metal bonding composition. The amino silane and sulphide silane are formulated in a ratio of 1:3 respectively, in an ethanol/water solution.

International Patent Publication No. WO2004/078867 to Lord Corporation describes a single coat solvent-based adhesive designed to bond thermoplastic elastomers containing an alkoxy silane/urethane adduct and a chlorinated polymer. Methods of synthesis and formulation are described within this patent document. U.S. Pat. No. 4,031,120 to Lord Corporation describes a composition comprising an isocyanate functional organosilane, in combination with a polyisocyanate and an aromatic nitroso compound. The resulting system is described as a one-coat adhesive for bonding a variety of elastomeric materials to metals and other substrates.

Canadian Patent No. 1,087,774 describes a composition for use in the production of composite rubber materials. The composition discloses a one-part composition comprising a vulcanisable polymer, a discrete aromatic nitroso compound and a discrete organic phosphonic acids (and partial esters thereof). Problematically, the toxic nitrosobenzene component is freely formulated within the composition.

Generally, it is desirable that bonding is achieved during a vulcanisation step like compression moulding, transfer moulding, injection moulding and autoclave heating, for example with steam or hot air. For example, semi-solid rubber can be injected into a mould. The semi-solid rubber is then cross-linked into a fully cured rubber and the bond with the substrate is formed at the same time.

Certain requirements of the curing system are desirable. These include, ease of processing, stability (for example avoiding sedimentation), ease of application, fast drying (to allow handling without fouling), good wetting properties, and good curing strengths. Curing should be achieved independently of the type of elastomer (rubber) employed and also independently of the type of substrate. It will be appreciated that some rubbers are blended materials and accordingly it is desirable that good curing is achieved with such blended materials. Suitably consistent curing is achieved under various process parameters. Durability is also desirable.

Notwithstanding the state of the art it would be desirable to provide compositions to bond polymeric substrates to a variety of substrates (such as metals, glass, quartz) that remedy some or all of the known deficiencies and/or provide alternatives to the existing technologies so that consumers have more possibilities from which to choose.

SUMMARY

The present invention provides for novel compounds, adhesive compositions comprising the compounds, and methods of bonding to polymeric substrates. Suitably, the polymer is one with diene and or allylic functionality within the polymer chain. The polymer may have allylic functionality within the polymer chain. For example, the polymer may be an elastomer, such as a natural or synthetic rubber. The synthetic rubber may be a nitrile butadiene rubber. The synthetic rubber may be a hydrogenated nitrile butadiene rubber (HNBR).

In a first aspect, the present invention provides for a compound comprising:

(a) at least one phosphonate moiety; or (b) at least one phosphinate moiety; and (c) at least one moiety selected from an aromatic nitroso or an aromatic nitroso precursor and combinations thereof.

Within the context of this specification the term aromatic nitroso moiety refers to an aromatic moiety having at least one nitroso group. Similarly, the term aromatic nitroso precursor moiety refers to any compound that is capable of being transformed into an aromatic nitroso moiety with at least one nitroso group. The term aromatic comprises both fused and non-fused aromatic rings. For example, a non-limiting selection of fused and non-fused aromatic nitroso moieties embraced by the present invention are detailed below:

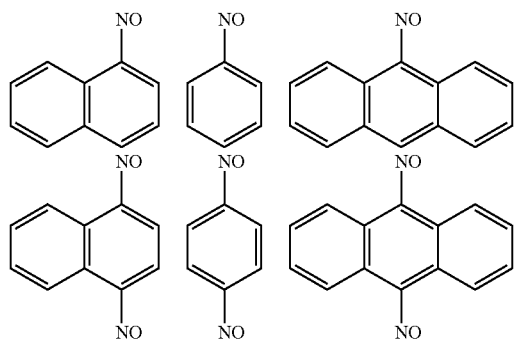

As will be appreciated by a person skilled in the art, the nitroso structures disclosed above may optionally be substituted one or more times, for example with at least one of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_6$-$C_{20}$ arylamine, $C_6$-$C_{20}$ arylnitroso, cyano, amino, hydroxy, halogen and combinations thereof. Such substitutions are possible provided there is no interference with effective bonding or curing of the compositions.

The aromatic nitroso precursor moiety may comprise any aromatic oxime, aromatic dioxime and combinations thereof. For example, the aromatic nitroso precursor moiety may be the mono- or dioxime of a compound selected from

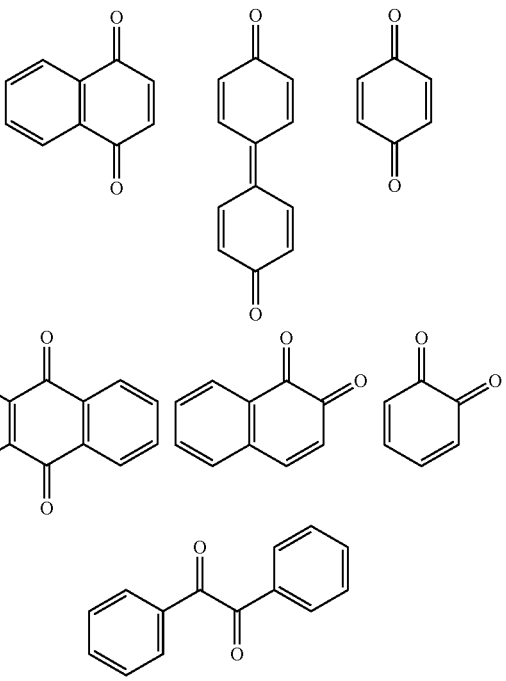

As will be appreciated by a person skilled in the art, the diketone structures disclosed above may optionally be substituted one or more times, for example with at least one of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_6$-$C_{20}$ arylamine, $C_6$-$C_{20}$ arylnitroso, cyano, amino, hydroxy, halogen and combinations thereof. Such substitutions are possible provided there is no interference with effective bonding or curing of the compositions. For example, provided there is no interference with the generation of an aromatic nitroso compound in-situ.

The at least one moiety selected from an aromatic nitroso or an aromatic nitroso precursor and combinations thereof may be selected from a nitrosobenzene or a nitrosobenzene precursor and combinations thereof. The nitrosobenzene moiety may be a mononitrosobenzene or a dinitrosobenzene. The nitrosobenzene precursor may be a mononitrosobenzene precursor or a dinitrosobenzene precursor. It will be appreciated that the nitrosobenzene precursor may form a nitrosobenzene structure in-situ. The nitrosobenzene precursor may be at least one of a quinone dioxime or a quinone oxime.

As will be appreciated by a person skilled in the art, references to nitrosobenzene and nitrosobenzene precursor moieties include nitrosobenzene and nitrosobenzene precursor moieties that may optionally be substituted one or more times with at least one of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_6$-$C_{20}$ arylamine, $C_6$-$C_{20}$ arylnitroso, cyano, amino, hydroxy, halogen and combinations thereof. Such substitutions are possible provided there is no interference with effective bonding or curing of the compositions. For example, provided there is no interference with the generation of a nitrosobenzene moiety in-situ.

Such structures may assist in the formation of desirable bonds to polymeric substrates, such as elastomers, for example substrates.

The phosphonate moiety may be of the structure:

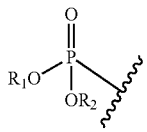

where $R_1$ and $R_2$ are the same or different and are selected from H, $C_1$-$C_{24}$ alkyl, and $C_3$-$C_{24}$ acyl.

$R_1$ and $R_2$ may be the same or different and may be selected from $C_1$-$C_4$ alkyl.

The phosphinate moiety may be of the structure:

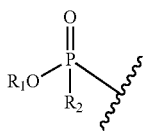

where $R_1$ is selected from H, $C_1$-$C_{24}$ alkyl, and $C_3$-$C_{24}$ acyl; and $R_2$ is selected from $C_1$-$C_{24}$ alkyl, and $C_3$-$C_{24}$ acyl; and $R_1$ and $R_2$ may be selected from $C_1$-$C_4$ alkyl.

In each of the above structures the squiggle indicates attachment to a moiety comprising an aromatic nitroso, an aromatic nitroso precursor or combinations thereof.

A compound according to the present invention may be embraced by the general structure:

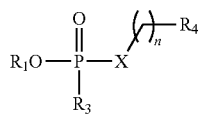

where X can be C, O, N, or S;

n can be 0-20;

$R_3$ can be $C_1$-$C_{24}$ alkyl, $C_3$-$C_{24}$ acyl or $OR_2$;

$R_1$ and $R_2$ can be the same or different and are selected from H, $C_1$-$C_{24}$ alkyl, and $C_3$-$C_{24}$ acyl; and $R_4$ may be a moiety comprising nitrosoaromatic, or a nitrosoaromatic precursor.

$R_1$, $R_2$ and $R_3$ can be the same or different and may be selected from $C_1$-$C_4$ alkyl. n may be 0 to 5. n may be 1 to 4. $R_4$ may be a moiety comprising nitrosobenzene, quinone dioxime or quinone oxime. X may be C, O or N. X may be C or O. X may be C. X may be O.

Structures for $R_4$ may be selected from (showing linkage through X):

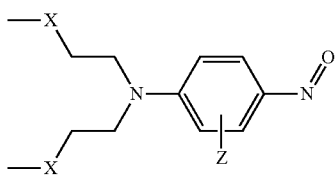

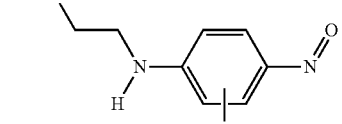

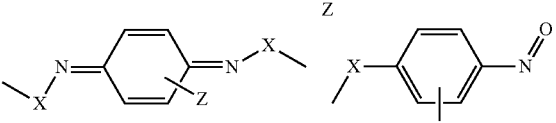

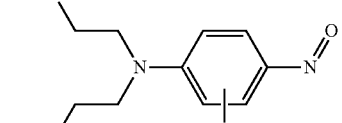

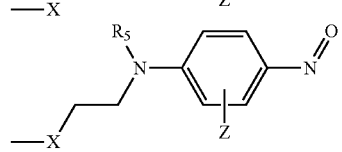

where $R_5$ can be $C_1$ to $C_{10}$ alkyl; and

Z indicates that the rings of the above structures can optionally be substituting mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further wherein the substituents can either be the same or different on each carbon atom of the ring. Such substitutions may be possible provided there is no interference with effective bonding or curing of the compositions. For example, provided there is no interference with the generation of a nitrosobenzene compound in-situ.

A compound according to the present invention may be of the general formula:

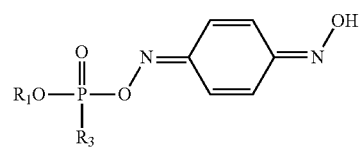

where $R_3$ can be $C_1$-$C_{24}$ alkyl, $C_3$-$C_{24}$ acyl or $OR_2$;

$R_1$ and $R_2$ can be the same or different and are selected from H, $C_1$-$C_{24}$ alkyl, and $C_3$-$C_{24}$ acyl.

$R_1$, $R_2$ and $R_3$ can be the same or different and may be selected from $C_1$-$C_4$ alkyl.

A compound according to the present invention may be of the following general structure;

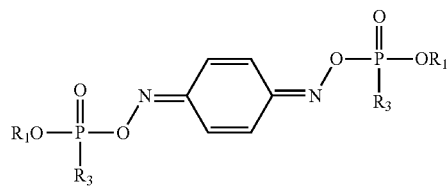

where $R_3$ can be $C_1$-$C_{24}$ alkyl, $C_3$-$C_{24}$ acyl or $OR_2$;

$R_1$ and $R_2$ can be the same or different and are selected from H, $C_1$-$C_{24}$ alkyl, and $C_3$-$C_{24}$ acyl.

$R_1$, $R_2$ and $R_3$ can be the same or different and may be selected from $C_1$-$C_4$ alkyl.

The invention provides for a polymer or co-polymer of a compound according to the present invention. In one embodiment, the invention further provides for an oligomer or a co-oligomer comprising:
(a) at least one phosphonate moiety;
(b) at least one phosphinate moiety; and
(c) at least one moiety selected from an aromatic nitroso or an aromatic nitroso precursor and combinations thereof, where a co-oligomeric compound is composed of different monomers.

The oligomer or a co-oligomer may have the following general structural formula:

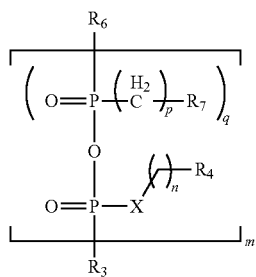

where m can be 1-100; n can be 0-20; p can be 1-10; q can be 0-50; and if q=0, m≧2;

$R_3$ and $R_6$ can be the same or different and may be selected from $C_1$-$C_{24}$ alkyl, $C_3$-$C_{24}$ acyl or $OR_2$;

$R_2$ can be selected from H, $C_1$-$C_{24}$ alkyl, and $C_3$-$C_{24}$ acyl; X can be C, O, N, or S;

$R_4$ may be a moiety comprising nitrosoaromatic, or a nitrosoaromatic precursor; and $R_7$ can be selected from acrylate, aldehyde, amino, anhydride, azide, maleimide, carboxylate, sulfonate, epoxide, ester functional, halogens, hydroxyl, isocyanate or blocked isocyanate, sulphur functional, vinyl and olefin functional, or polymeric structures.

$R_2$, $R_3$ and $R_6$ can be the same or different and may be selected from $C_1$-$C_4$ alkyl. n may be 0 to 5. n may be 1 to 4. p may be 1 to 5. q may be 1 to 5. $R_4$ may be a moiety comprising nitrosobenzene, quinone dioxime or quinone oxime. X may be C, O or N. X may be C or O. X may be C. X may be O.

Compounds according to the present invention may find utility in applications for bonding to polymeric substrates. Suitably, the polymer is one with diene and or allylic functionality within the polymer chain. The polymer may have allylic functionality within the polymer chain. The polymer may be an elastomer, for example a rubber (natural or synthetic). The synthetic rubber may be a nitrile butadiene rubber. The synthetic rubber may be a hydrogenated nitrile butadiene rubber (HNBR). Compounds of the present invention can be easily applied at the interface of bonding surfaces and assist in developing strong and durable bonds during the curing process.

Compounds according to the present invention may result in a number of advantages. Compounds and formulations as so provided may have reduced toxicity as compared to conventional dinitrosobenzene formulations. Additionally, compounds and the present invention may achieve excellent bond strengths when bonding to rubber substrates.

The compounds of the present invention may be utilised to bond a polymeric substrate as defined above to a second substrate. The second substrate may be a metal or a hydroxylated surface.

As used herein the term hydroxylated surface refers to any substrate with a surface comprising an atom bonded to a hydroxy group. Suitable non-limiting examples include, a hydrous metal oxide, glass substrates comprising surface Si—OH bonds or clay substrates comprising surface Al—OH bonds. Suitable hydroxylated surfaces include those of silicates, aluminates, germanates and combinations thereof. The hydroxylated surface may be a silicate, an aluminate or combinations thereof. As used herein, the term silicate refers to substrates comprising Si—OH bonds. The term aluminate refers to substrates having Al—OH bonds and the term germinate refers to substrates having Ge—OH bonds. As used herein, hydroxylated surface also comprises substrates primed with hydroxylated materials, for example primed with a silicate, aluminate, germanate and combinations thereof.

For example, the hydroxylated surface may be glass such as glass fibres, quartz, clays, talcs, zeolites, porcelains, ceramics, and silicon substrates such as silicon wafers and combinations thereof.

Many different metals may be bonded using the compounds of the present invention. Suitable metals include, but are not limited to, zinc and zinc alloys such as zinc-nickel and zinc-cobalt alloys, metal substrates having zinc-containing coatings, steel and in particular cold rolled and carbon steel, aluminium and aluminium alloys, copper and copper alloys such as brass, and tin and tin alloys including metal substrates having tin-containing coatings.

The compounds of the present invention may assist in the formation of polymer to glass bonds or metal bonds. The polymer may be an elastomer such as a natural or synthetic rubber. The synthetic rubber may be a nitrile butadiene rubber. The synthetic rubber may be HNBR. The compounds can be easily applied at the interface between the polymer and the glass or metal substrate and may assist in developing strong and durable bonds during the curing process.

Accordingly, in a further aspect the present invention provides a composition for bonding substrates together, the composition comprising:
i) at least one compound according to the present invention.

The composition of the present invention may further comprise:
ii) a suitable carrier vehicle for the compound.

It will be appreciated that any suitable carrier vehicle may be utilised. It is particularly desirable that the carrier vehicle should be environmentally friendly.

Compositions of the present invention may be one-part compositions. Compositions of the present invention may be two-part compositions. The so-described compositions may result in a number of advantages. For example, a one-part adhesive system may be formulated. Such systems are readily applied to substrates in a single step using convenient and conventional techniques, for example spraying or dipping. Compositions as so provided may have reduced toxicity as compared to conventional dinitrosobenzene formulations there are no free (or untethered) nitrosobenzene compounds formulated in the composition. Compositions as so provided can also achieve excellent bond strengths to polymeric materials, such as elastomers, for example rubbers (natural or synthetic).

Compositions of the present invention may find utility in any application where it is desirable to form an aromatic nitroso moiety in-situ. Similarly, compositions of the present invention may find utility in any application where it is desirable to form an aromatic dinitroso moiety in-situ. It will be appreciated that within these compositions the compound can react in-situ to form a nitrosobenzene moiety. It is also contemplated that the compound can react in-situ to form a dinitrosobenzene moiety. For example, for particularly good bonding it may be desirable for the compound to react in-situ to form a para-nitrosophenol moiety.

The compound of the present invention (also referred to as a nitrosophosphonate or a nitrosophosphinate) may be present in an amount of 1 to 20% w/w of the total composition. Suitably, the compound may be present in an amount of 1 to 15% w/w, for example 4 to 12% w/w. The compound may be present in 6% w/w of the total composition.

Compositions of the present invention may optionally comprise one or more silanes. These silanes may be of the general formula:

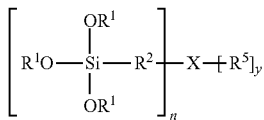

where n is either 1 or 2;
y=(2-n) each $R_1$ can be selected from $C_1$-$C_{24}$ alkyl or $C_2$-$C_{24}$ acyl;
each $R_2$ can be selected from $C_1$-$C_{30}$ aliphatic groups, substituted or unsubstituted $C_6$-$C_{30}$ aromatic groups;
$R_5$ can be selected from hydrogen, $C_1$-$C_{10}$ alkylene, alkylene optionally substituted with one or more amino groups, $C_2$-$C_{10}$ alkenylene optionally substituted with one or more amino groups, $C_6$-$C_{10}$ arylene, or $C_7$-$C_{20}$ alkarlyene;
X—$R_5$ is optional and X is either:

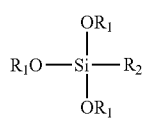

where each $R_3$ can be selected from hydrogen, $C_1$-$C_{30}$ aliphatic groups, or $C_6$-$C_{30}$ aromatic groups;
$R_4$ can be selected from $C_1$-$C_{30}$ aliphatic groups, or $C_6$-$C_{30}$ aromatic groups; where when n=1, at least one of the $R_3$ and the $R_5$ is not hydrogen.

In one embodiment, X—$R_5$ is present. $R_1$ can be selected from $C_1$-$C_{24}$ alkyl, $R_2$ can be selected from $C_1$-$C_{30}$ aliphatic groups, X can be N—$R_3$ and $R_5$ can be selected from hydrogen or $C_1$-$C_{10}$ alkylene. As will be appreciated, when X—$R_5$ is absent the silane may be of the general formula (where $R_1$ and $R_2$ are as defined above):

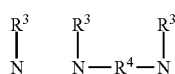

Preferred silanes include bis-silyl silanes such as those having two trisubstituted silyl groups. The substituents may be individually chosen from $C_1$-$C_{20}$ alkoxy, $C_6$-$C_{30}$ aryloxy and $C_2$-$C_{30}$ acyloxy. Suitable bis-silyl silanes for use within the compositions of the present invention include:

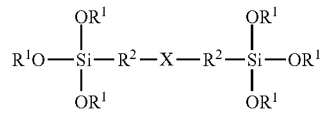

where each $R_1$ can be selected from $C_1$-$C_{24}$ alkyl or $C_2$-$C_{24}$ acyl;
each $R_2$ can be selected from the group consisting $C_1$-$C_{20}$ aliphatic groups, or $C_6$-$C_{30}$ aromatic groups;
X is optional and is either:

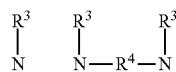

where each $R_3$ can be selected from hydrogen, $C_1$-$C_{20}$ aliphatic groups, or $C_6$-$C_{30}$ aromatic groups; and
$R_4$ can be selected from $C_1$-$C_{20}$ aliphatic groups or $C_6$-$C_{30}$ aromatic groups.

In one embodiment, X is present. $R_1$ can be selected from $C_1$-$C_{24}$ alkyl, $R_2$ can be selected from $C_1$-$C_{30}$ aliphatic groups, and X can be N—$R_3$. As will be appreciated, when X is absent the bis-silane may be of the general formula (where $R_1$ and $R_2$ are as defined above):

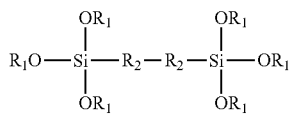

Examples of some bis-silyl aminosilanes embraced by the present invention include: bis-(trimethoxysilylpropyl)amine, bis-(triethoxysilylpropyl)amine, bis-(triethoxysilylpropyl) ethylene diamine, N-[2-(vinylbenzylamino)ethyl]-3-aminopropyltrimethoxy silane, and aminoethyl-aminopropyltrimethoxy silane.

Such silanes may be included in the range from 1:3 to 3:1 (stoichiometrically) relative to the compounds of the present invention (i.e., a nitrosophosphonate or a nitrosophosphinate). The addition of silanes to the composition of the present invention can result in excellent bonding to rubber substrates.

The silane may be present in an amount of 1 to 10% w/w of the total composition. Suitably, the silane may be present in an amount of 1 to 5% w/w, for example 1 to 3% w/w. The silane may be present in about 3% w/w of the total composition.

The compound of the present invention may be substantially hydrolysed in the composition of the present invention. A carrier comprising water may allow for hydrolysis of the compound comprising the at least one phosphonate or phosphinate moiety. As used herein hydrolysis of the compound refers to hydrolysis of an alkoxy (or acyloxy) group of the phosphonate or phosphinate moiety, i.e. hydrolysis of any alkoxy moiety to yield a hydroxy moiety. At least one alkoxy moiety in the compound may be hydrolysed to ensure good bonding. Advantageously, hydrolysis of the compound prior to bonding may result in improved adhesion. Hydrolysis of the compound prior to bonding may result in improved bond strengths. Hydrolysis of the compound prior to bonding may result in improved bond strengths in bonding a polymeric substrate having diene and or allylic functionality within the polymer chain to a metal or hydroxylated surface.

The carrier of the composition of the present invention may comprise between 0.1-100% w/w water. The carrier of the composition of the present invention may comprise between 0.5-50% w/w water. The carrier of the composition of the present invention may comprise between 1-20% w/w water. Suitably, a carrier comprising about 5% w/w water may substantially hydrolyse the compound of the present invention.

The carrier may further comprise an organic solvent. Desirably, the organic solvent is miscible with water. This allows for efficient dissolution of and hydrolysis of the compound according to the present invention. The organic solvent may be selected from the group consisting of alcohols, carboxylic acids, acetone, acetonitrile, and tetrahydrofuran. The organic solvent may be an alcohol. Suitable alcohols include, without limitation, methanol, ethanol, propanol and isomers thereof, butanol and isomers thereof, and pentanol and isomers thereof.

The carrier may consist of water and an alcohol. An alcohol:water carrier may provide for dissolution of the compound of the present invention in the carrier, thereby enabling uniform application of the compound as a film or coating to a target substrate. Uniform application of the compound as part of a composition may result in improved bonding.

The composition of the present invention may further comprise an acid. Suitable acids include organic acids. For example, acetic acid, oxalic acid, formic acid, and propionic acid.

The provision of heat may aid in the hydrolysis of the phosphonate/phosphinate moiety of the compound of the present invention. The composition may be heated to a temperature between 30-100° C. Suitably, the composition may be heated to a temperature between 40-60° C. The composition may be heated to 50° C. The composition may be heated for between 1-2 hours. The composition may be heated for up to 2 hours. The composition may be applied directly to the target substrate. The composition may be cooled prior to application to the target substrate.

The compositions of the present invention may further comprise conventional additives such as fillers, pigments, stabilisers, moisture scavengers, etc., subject to said additives not interfering with effective curing of the compositions. The composition may comprise carbon blacks. The carbon blacks may be acidic or basic. The composition may comprise silica. The composition may comprise polyvinyl butyral resin.

Compositions according to the present invention may find utility in applications for bonding to polymeric substrates. Suitably, the polymer is one with diene and or allylic functionality within the polymer chain. The polymer may have allylic functionality within the polymer chain. The polymer may be an elastomer, for example a rubber (natural or synthetic). The synthetic rubber may be a nitrile butadiene rubber. The synthetic rubber may be a hydrogenated nitrile butadiene rubber (HNBR).

The compositions of the present invention may be utilised to bond a polymeric substrate as defined above to a second substrate. The second substrate may be a metal or a hydroxylated surface as defined herein.

Compositions according to the present invention may result in a number of advantages. Compounds and formulations as so provided may have reduced toxicity as compared to conventional dinitrosobenzene formulations, as no free or untethered nitrosobenzene compounds are formulated within the composition. Additionally, compounds and the present invention may achieve excellent bond strengths when bonding to rubber substrates.

It will be appreciated by a person skilled in the art that the curable compositions of the present invention may additionally comprise conventional additives such as fillers, pigments, stabilisers, and moisture scavengers, provided that the additives do not interfere with effective curing of the compositions.

In contrast to conventional systems the adhesive systems of the present invention can be applied to the unvulcanised rubber, prior to vulcanisation and bond formation, and upon subsequent vulcanization a bond results. This means that the adhesive system may be applied to either the rubber or the metal or the hydroxylated surface. Conventional systems do not form a bond if applied in this manner. The adhesive systems of the present invention can be applied to an unvulcanised rubber substrate (as distinct from a metal or glass substrate), prior to vulcanisation and bond formation, and upon subsequent vulcanization a bond results. The composition may be applied to a metal or a hydroxylated surface. This means that the adhesive system may be applied to either the polymeric substrate such as a rubber or a metal or glass substrate. Conventional systems do not form a bond if applied in this manner.

The rubber substrate may be vulcanised or crosslinked prior to bonding to the metal or hydroxylated surface. The rubber substrate may be vulcanised or crosslinked concurrently with bonding to the metal surface.

In a further aspect, the present invention relates to a process for bonding two substrates together comprising:

a) applying a composition according to the present invention to at least one of the substrates and mating the substrates together so as to form a bond therebetween.

A first substrate may comprise a polymer. The polymer may comprise alkene and/or allylic functionality within the polymer chain. For example, diene and/or allylic functionality may be present within the polymer chain. Suitably, the polymer may comprise allylic functionality. Suitable polymers may include elastomers. Suitable elastomers may comprise natural or synthetic rubbers. The synthetic rubber may be a nitrile butadiene rubber. The synthetic rubber may be HNBR. The polymer may be a $C_2$-$C_{1,000,000}$ polymer, such as a $C_2$-$C_{10,000}$ polymer.

The second substrate may be a metal or a hydroxylated surface as defined herein. The second substrate may be a metal.

The method of the present invention may additional comprise the step of:

b) substantially hydrolysing the compound of the present invention.

At least one alkoxy (or acyloxy) moiety in the compound may be hydrolysed to ensure good bonding. As will be appreciated by a person skilled in the art, the order of steps a) and b) may be reversed. For example, the product may be applied to at least one substrate and then hydrolysed, or the product may be hydrolysed prior to application to the at least one substrate.

The step of substantially hydrolysing the compound of the present invention may comprise heating the composition to encourage hydrolysis of the phosphonate/phosphinate moiety of the compound of the present invention. The composition may be heated to a temperature between 30-100° C. Suitably, the composition may be heated to a temperature between 40-60° C. The composition may be heated to 50° C. The composition may be heated for between 1-2 hours. The composition may be heated for up to 2 hours. The composition may be applied directly to the target substrate. The composition may be cooled prior to application to the target substrate.-

The method may further comprise the step of heating subsequent to mating the first and second substrates. Advantageously, heating may increase the rate of bond formation. Heating may improve bond strength.

The composition may be applied to a target substrate as a thin film or coating. This may allow for uniform (or even) application of the composition to the target substrate. Uniform application of the composition to a target substrate may allow for improved bonding.

The method of the present invention may additionally comprise the step of cleaning, for example abrasively cleaning, such as blasting, for example grit-blasting the substrate prior to application of the composition thereto.

According to the method of the present invention a first substrate, for example, may be a polymer. The polymer may comprise alkene and/or allylic functionality within the polymer chain. For example, diene and/or allylic functionality may be present within the polymer chain. Suitably, the polymer may comprise allylic functionality. Suitable polymers may include elastomers. Suitable elastomers may comprise natural or synthetic rubbers. The synthetic rubber may be a nitrile butadiene rubber. The synthetic rubber may be HNBR. The polymer may be a $C_2$-$C_{1,000,000}$ polymer, such as a $C_2$-$C_{100,00}$ polymer.

The second substrate may be a metal or a hydroxylated surface as defined herein. The second substrate may be a metal.

In bonding, the phosphinate/phosphonate moiety of the compound will anchor to the surface of the metal or the hydroxylated surface. The moiety selected from an aromatic nitroso or an aromatic nitroso precursor will generally become anchored to the polymer, for example a rubber material. Accordingly, each end of the molecule is functionalised and assists in bonding the materials together with a strong and durable bond.

Thus, a metal coated with an adhesive composition as so described may be adhered to a polymeric material, for example a rubber composition, by applying the polymeric material in an uncured state onto the metal coated with the adhesive composition and curing the polymeric material thereon to bond it to the metal. In the case of a rubber polymeric material the uncured rubber may be vulcanized via heat and pressure over a period of time to cure the rubber, resulting in bonding of the rubber to the metal.

Suitable polymers are those capable of reacting with nitroso groups so as to provide cross-links therebetween. Such a reaction produces a variety of cross-links, for example between the nitroso group and a rubber material. The materials of the invention are thought to reduce free nitroso groups as the nitroso group is within a molecular structure. In the reaction of the nitroso group and the phosphonate/phosphinate, the nitroso may react with allylic functionality within a natural rubber while the phosphonate/phosphinate forms a bond with the second substrate, such as a hydroxylated surface or metal.

Excellent adhesion between polymeric materials, such as elastomeric materials, for example rubber compositions, and metals or hydroxylated surfaces, may be realized through the use of the compounds and compositions as so described.

In a further aspect the present invention provides for an assembly of at least two substrates bound together by an adhesive composition according to the present invention.

In yet a further aspect the present invention provides for a cure product comprising a substrate and a composition according to the present invention.

Where suitable, it will be appreciated that all optional features of one embodiment of the invention may be combined with optional features of another/other embodiment(s) of the invention.

DETAILED DESCRIPTION

It should be readily apparent to one of ordinary skill in the art that the examples disclosed herein below represent generalised examples only, and that other arrangements and methods capable of reproducing the invention are possible and are embraced by the present invention.

It is envisaged that compounds according to the present invention may be synthesised according to the following synthetic transformations.

Nucleophilic Substitution of Diphenylphosphoryl Azide

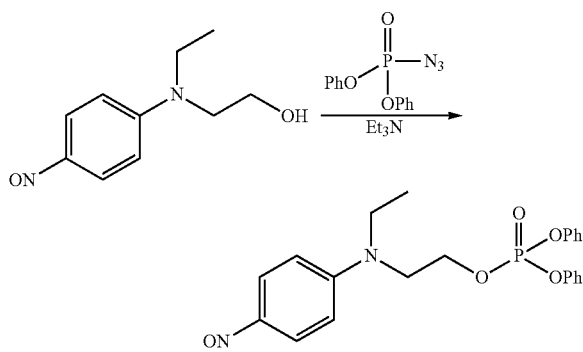

Michaelis-Arbuzov Reaction

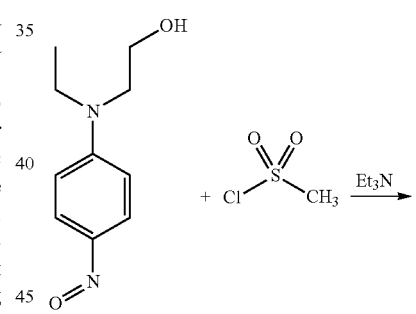

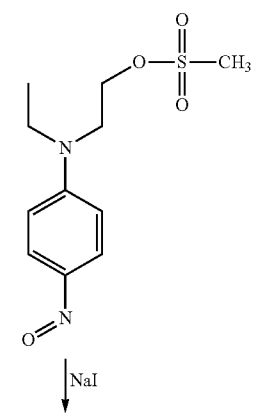

-continued

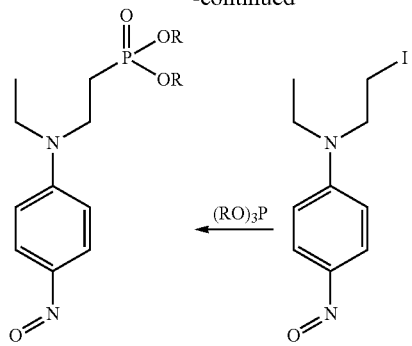

Adhesive/bonding compositions comprising the compounds of the present invention could be formulated as set out in Table 1 below.

TABLE 1

| Component | Composition Range % by weight |
|---|---|
| Nitroso phosphonate or phosphinate molecule | 4-14% |
| Bis(trimethoxysilylpropyl)amine | 0.5-5% |
| Pergut[a] | 6-16% |
| Xylene[b] | 60-80% |
| Isopropanol[b] | 6-16% |

[a]Chlorinated Natural Rubber (Bayer Material Science);
[b]Used as received from supplier It is envisaged that adhesive or bonding compositions comprising the nitrosophosphonate or nitrosophosphinate molecules according to the present invention could be utilised to bond materials (for example plastics or metals) to rubber substrates. Suitable rubber substrates include both natural and synthetic rubber compositions as outlined in Tables 2 & 3 below.

The bonding compositions comprising the nitrosophosphonate or nitrosophosphinate molecules may be applied to (metal) substrates by either a dipping, spraying or brush method to ensure an even coverage, preferably after the substrate has been cleaned.

A layer of uncured rubber may then be placed on the substrate to which the bonding composition has been placed and cured in a standard hydraulic vulcanisation press for a period of time specified by the rubber's cure profile. In the case of the natural rubber composition illustrated in Table 2, one would expect the rubber to be cured for 20 minutes at 150° C. under a pressure of 20-30 Tonnes, to ensure intimate contact of the surfaces being bonded and the adhesive.

TABLE 2

| Natural Rubber Composition | |
|---|---|
| Ingredient | Parts by weight |
| Natural Rubber[a] | 100 |
| Zinc Oxide | 3.5 |
| Stearic Acid | 2 |
| Carbon Black[b] | 40 |
| Naphthenic Oil (low viscosity)[c] | 5 |
| 1,2-Dihydro-2,2,4-Trimethylquinoline[d] | 2 |
| N-(1,3-dimethylbutyl)-N'-phenyl-p-phenylenediamine[e] | 1 |
| Hydrocarbon Waxes[f] | 2 |
| CBS[g] | 0.7 |
| Sulphur | 2.5 |

[a]NR SMR CV 60;
[b]SRF N762 black;
[c]Oil Strukthene 410;
[d]Flectol H;
[e]Santoflex 13 (HPPD);
[f]Sunproof Improved Wax;
[g]Vulcanisation accelerator, N-Cyclohexyl-2-benzothiazole.

TABLE 3

| EPDM Synthetic Rubber Composition | |
|---|---|
| Ingredient | Parts by weight |
| Ethylene-Propylene-Ethylidene Norbornene (7.8% diene)[a] | 25 |
| Ethylene-Propylene-Ethylidene Norbornene (9.0% diene)[b] | 72.5 |
| Ethylene-Propylene-Dicyclopentadiene (10.5% diene)[c] | 25 |
| Carbon Black | 70 |
| Calcium Oxide | 10 |
| Stearic Acid | 1 |
| Zinc Oxide | 5 |
| Dicumyl peroxide[d] | 3.75 |
| Polyethylene Glycol[e] | 4.5 |

[a]Buna EP G 3850;
[b]Buna EP G 3963;
[c]Trilene 65;
[d]Dicup 40C;
[e]Carbowax 400

The invention claimed is:
1. A compound comprising:
(a) at least one phosphonate moiety; or
(b) at least one phosphinate moiety; and
(c) at least one moiety selected from an aromatic nitroso or an aromatic nitroso precursor and combinations thereof wherein the compound is of the general formula:

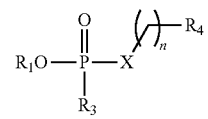

wherein X can be C, O, N, or S;
n can be 0-20;
$R_3$ can be $C_1$-$C_{24}$ alkyl, $C_3$-$C_{24}$ acyl or $OR_2$;
$R_1$ and $R_2$ can be the same or different and are selected from the group consisting of H, $C_1$-$C_{24}$ alkyl, and $C_3$-$C_{24}$ acyl; and
$R_4$ is selected from the group consisting of (showing linkage through X):

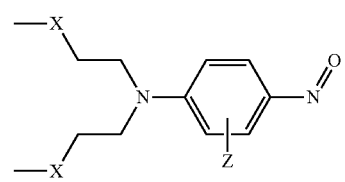

-continued

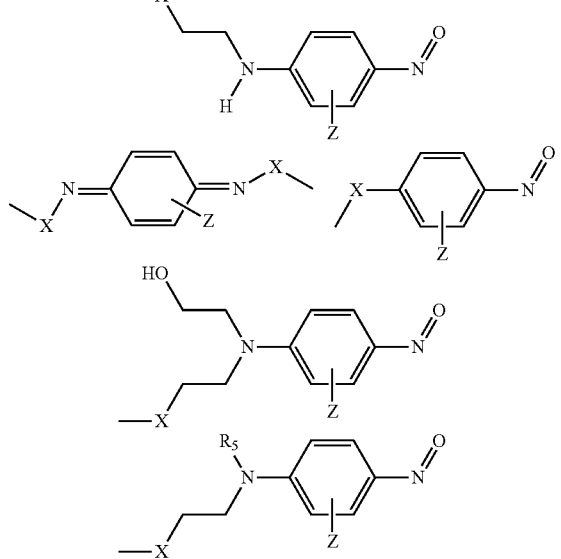

wherein $R_5$ can be $C_1$ to $C_{10}$ alkyl; and

Z indicates that the rings of the above structures can optionally be mono-, di-, tri- or tetrasubstituted with the group consisting of $C_1$-$C_{20}$alkyl, $C_3$-$C_{20}$ cycloalkyl, $C_1$-$C_{20}$ alkoxy, $C_3$-$C_{20}$ aralkyl, $C_3$-$C_{20}$ alkaryl, $C_5$-$C_{20}$ arylamine, $C_5$-$C_{20}$ arylnitroso, amino, hydroxy, halogen and combinations thereof, and further wherein the substituents can either be the same or different on each carbon atom of the ring.

2. A compound of the general formula:

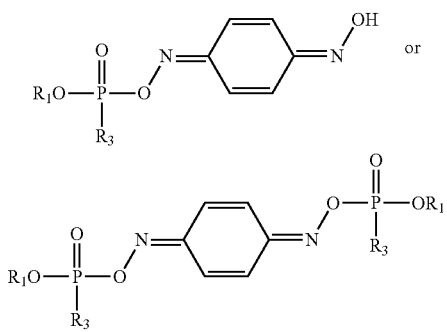

wherein $R_3$ can be $C_1$-$C_{24}$ alkyl, $C_3$-$C_{24}$ acyl or $OR_2$;

$R_1$ and $R_2$ can be the same or different and are selected from the group consisting of H, $C_1$-$C_{24}$ alkyl, and $C_3$-$C_{24}$ acyl.

3. An oligomer or co-oligomer of a compound comprising
(a) at least one phosphonate moiety; or
(b) at least one phosphinate moiety; and
(c) at least one moiety selected from an aromatic nitroso or an aromatic nitroso precursor and combinations thereof.

4. A polymer or co-polymer of a compound comprising
(a) at least one phosphonate moiety; or
(b) at least one phosphinate moiety; and
(c) at least one moiety selected from an aromatic nitroso or an aromatic nitroso precursor and combinations thereof.

5. An oligomer or co-oligomer according to claim 2 of the following general formula:

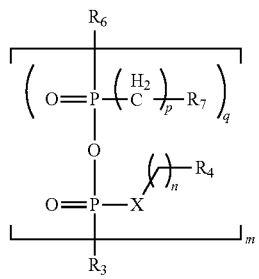

wherein m can be 1-100; n can be 0-20; p can be 1-10; q can be 0-50; and if q=0, m≧2;

$R_3$ and $R_6$ can be the same or different and may be selected from $C_1$-$C_{24}$ alkyl, $C_3$-$C_{24}$ acyl or $OR_2$;

$R_2$ can be selected from the group consisting of H, $C_1$-$C_{24}$ alkyl, and $C_3$-$C_{24}$ acyl; X can be C, O, N, or S;

$R_4$ may be a moiety comprising nitrosoaromatic, or a nitrosoaromatic precursor; and $R_7$ can be selected from the group consisting of acrylate, aldehyde, amino, anhydride, azide, maleimide, carboxylate, sulfonate, epoxide, ester functional, halogens, hydroxyl, isocyanate or blocked isocyanate, sulphur functional, vinyl and olefin functional, or polymeric structures.

6. A composition for bonding substrates together, the composition comprising:
i) at least one compound comprising
(a) at least one phosphonate moiety; or
(b) at least one phosphinate moiety; and
(c) at least one moiety selected from an aromatic nitroso or an aromatic nitroso precursor and combinations thereof, and
ii) a silane.

7. A composition according to claim 6 wherein the silane is an amino silane.

8. A process for bonding two substrates together comprising:
a) applying a composition comprising:
at least one compound comprising
(a) at least one phosphonate moiety; or
(b) at least one phosphinate moiety; and
(c) at least one moiety selected from an aromatic nitroso or an aromatic nitroso precursor and combinations thereof to at least one of the substrates and mating the substrates together so as to form a bond therebetween.

9. A process according to claim 8 further comprising the step of heating subsequent to mating the first and second substrates.

10. A process according to claim 8 further comprising the step of abrasively cleaning at least one of the substrates prior to application of the composition thereto.

11. A process according to claim 8 wherein the first substrate is a polymer and the second substrate is a metal or a hydroxylated surface.

12. An assembly of at least two substrates bound together by an adhesive composition comprising:
at least one compound comprising
(a) at least one phosphonate moiety; or
(b) at least one phosphinate moiety; and (c) at least one moiety selected from an aromatic nitroso or an aromatic nitroso precursor and combinations thereof.

13. A cure product comprising a substrate and a composition comprising:
   at least one compound comprising
   (a) at least one phosphonate moiety; or
   (b) at least one phosphinate moiety; and
   (c) at least one moiety selected from an aromatic nitroso or an aromatic nitroso precursor and combinations thereof.

* * * * *

UNITED STATES PATENT AND TRADEMARK OFFICE
CERTIFICATE OF CORRECTION

PATENT NO. : 8,524,814 B2  
APPLICATION NO. : 13/446680  
DATED : September 3, 2013  
INVENTOR(S) : Nigel Fay et al.

Page 1 of 1

It is certified that error appears in the above-identified patent and that said Letters Patent is hereby corrected as shown below:

In the Specification

Column 9, Line 32: After "C1-C10 alkylene", insert -- C1-C10 --.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*